United States Patent
Perszyk

(10) Patent No.: US 11,337,806 B2
(45) Date of Patent: May 24, 2022

(54) MITRAL VALVE DELIVERY DEVICE

(71) Applicant: St. Jude Medical, Cardiology Division, Inc., St. Paul, MN (US)

(72) Inventor: Brian Joseph Perszyk, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 266 days.

(21) Appl. No.: 16/816,984

(22) Filed: Mar. 12, 2020

(65) Prior Publication Data

US 2020/0205973 A1 Jul. 2, 2020

Related U.S. Application Data

(62) Division of application No. 15/592,737, filed on May 11, 2017, now Pat. No. 10,624,740.

(Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/9517* (2020.05);
(Continued)

(58) Field of Classification Search
CPC .... A61F 2/2436; A61F 2/2418; A61F 2/9517; A61F 2210/0014; A61F 2220/0008
See application file for complete search history.

(56) References Cited

U.S. PATENT DOCUMENTS 5,891,193 A 4/1999 Robinson et al.
6,132,458 A 10/2000 Staehle et al.
(Continued)

FOREIGN PATENT DOCUMENTS

EP 0657147 A2 6/1995
WO 2010042950 A2 4/2010
(Continued)

OTHER PUBLICATIONS

European Search Report for EP Application No. 18195359.7, dated Jan. 22, 2019.
(Continued)

*Primary Examiner* — Jing Rui Ou
(74) *Attorney, Agent, or Firm* — Lerner, David, Littenberg, Krumholz & Mentlik, LLP

(57) ABSTRACT

A method of delivering a collapsible prosthetic heart valve may include providing a delivery device having a catheter assembly and an operating handle. The catheter assembly may include a compartment adapted to receive the valve and a slidable distal sheath. The operating handle may include a housing and first and second lead screws each movable in first and second opposite longitudinal directions. The method may include loading the valve into the compartment and covering the compartment and the valve with proximal and distal segments of the distal sheath. The method may include inserting the catheter assembly into the patient, and partially deploying the valve by moving the first lead screw in the first longitudinal direction. The method may include fully deploying the valve by simultaneously continuing movement of the first lead screw in the first longitudinal direction and moving the second lead screw in the second longitudinal direction.

10 Claims, 11 Drawing Sheets

Related U.S. Application Data

(60) Provisional application No. 62/336,112, filed on May 13, 2016.

(52) U.S. Cl.
CPC .............. *A61F 2210/0014* (2013.01); *A61F 2220/0008* (2013.01)

(56) References Cited

U.S. PATENT DOCUMENTS

| | | | |
|---|---|---|---|
| 6,395,017 | B1 | 5/2002 | Dwyer et al. |
| 7,938,851 | B2 * | 5/2011 | Olson .................... A61F 2/966 |
| | | | 623/1.11 |
| 8,475,523 | B2 | 7/2013 | Duffy |
| 8,814,931 | B2 | 8/2014 | Wang et al. |
| 9,192,469 | B2 | 11/2015 | Mearns et al. |
| 10,517,722 | B2 | 12/2019 | Passman et al. |
| 10,631,984 | B2 | 4/2020 | Nyuli et al. |
| 2002/0120323 | A1 | 8/2002 | Thompson et al. |
| 2003/0191516 | A1 | 10/2003 | Weldon et al. |
| 2004/0127912 | A1 | 7/2004 | Rabkin et al. |
| 2005/0137692 | A1 | 6/2005 | Haug et al. |
| 2005/0182486 | A1 | 8/2005 | Gabbay |
| 2006/0259135 | A1 | 11/2006 | Navia et al. |
| 2006/0282150 | A1 | 12/2006 | Olson et al. |
| 2006/0287718 | A1 | 12/2006 | Bicer |
| 2007/0162107 | A1 | 7/2007 | Haug et al. |
| 2007/0239271 | A1 | 10/2007 | Nguyen |
| 2008/0071363 | A1 | 3/2008 | Tuval et al. |
| 2009/0054976 | A1 | 2/2009 | Tuval et al. |
| 2009/0099530 | A1 | 4/2009 | Adams et al. |
| 2010/0057185 | A1 | 3/2010 | Melsheimer et al. |
| 2010/0121434 | A1 | 5/2010 | Paul et al. |
| 2010/0262231 | A1 | 10/2010 | Tuval et al. |
| 2010/0312333 | A1 | 12/2010 | Navia et al. |
| 2011/0137397 | A1 * | 6/2011 | Chau .................... A61F 2/246 |
| | | | 623/1.11 |
| 2011/0295216 | A1 | 12/2011 | Miller |
| 2012/0083874 | A1 | 4/2012 | Dale et al. |
| 2013/0023868 | A1 | 1/2013 | Worrell et al. |
| 2013/0274870 | A1 | 10/2013 | Lombardi et al. |
| 2013/0297011 | A1 | 11/2013 | Morris et al. |
| 2014/0046428 | A1 | 2/2014 | Cragg et al. |
| 2014/0371844 | A1 | 12/2014 | Dale et al. |
| 2015/0230955 | A1 | 8/2015 | Farag Eells et al. |
| 2015/0238315 | A1 * | 8/2015 | Rabito .................. A61F 2/2439 |
| | | | 623/2.11 |
| 2016/0317301 | A1 * | 11/2016 | Quadri .............. A61M 25/0067 |
| 2017/0165064 | A1 | 6/2017 | Nyuli et al. |

FOREIGN PATENT DOCUMENTS

| | | |
|---|---|---|
| WO | 2011150399 A1 | 12/2011 |
| WO | 2012127309 A1 | 9/2012 |
| WO | 2012178115 A2 | 12/2012 |
| WO | 2013028387 A2 | 2/2013 |
| WO | 2013059747 A1 | 4/2013 |

OTHER PUBLICATIONS

International Search Report and Written Opinion for Application No. PCT/US2014/042914 dated Nov. 14, 2014.

International Search Report for Application No. PCT/US2016/022748 dated Aug. 8, 2016.

Partial International Search Report for Application No. PCT/US2014/042914 dated Oct. 21, 2014.

International Search Report for Application No. PCT/US2017/032071 dated Jul. 5, 2017, 4 pages.

* cited by examiner

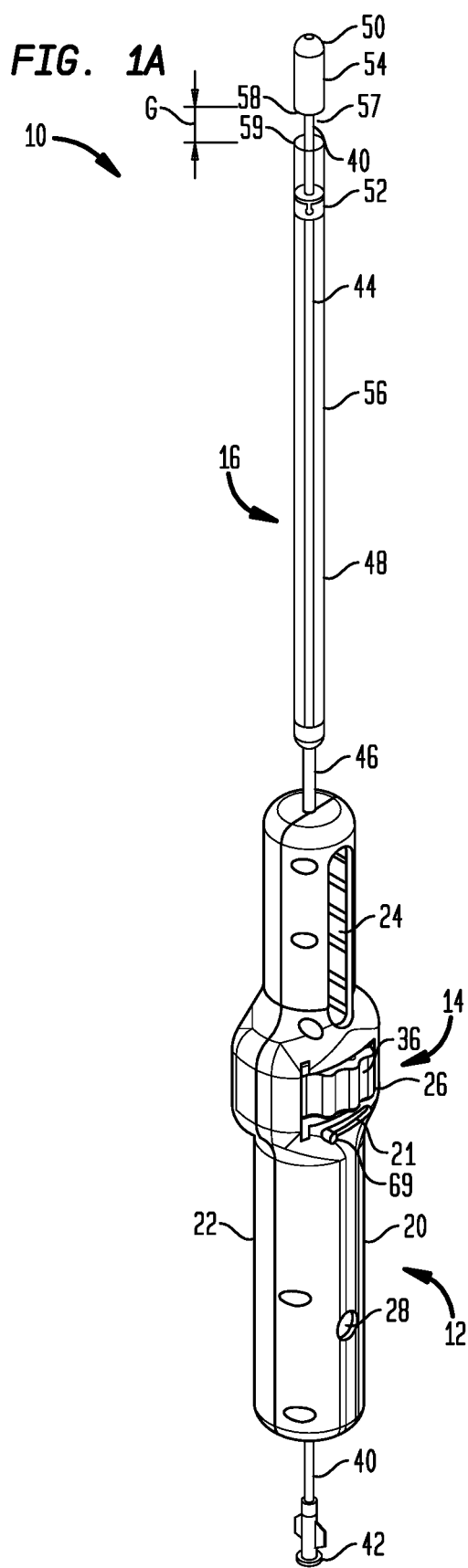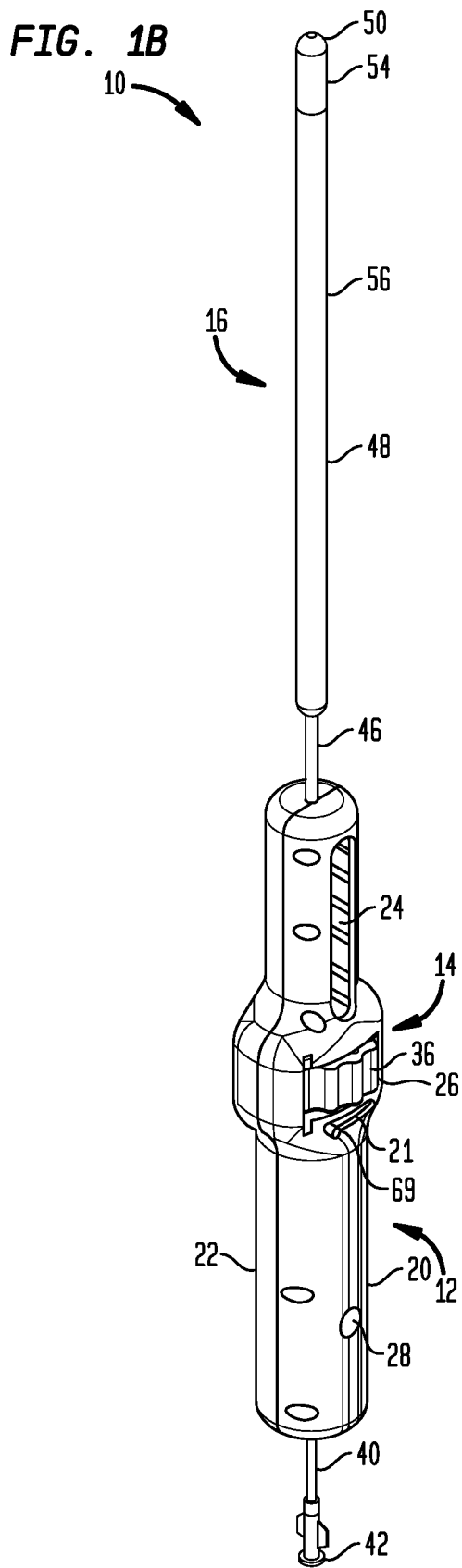

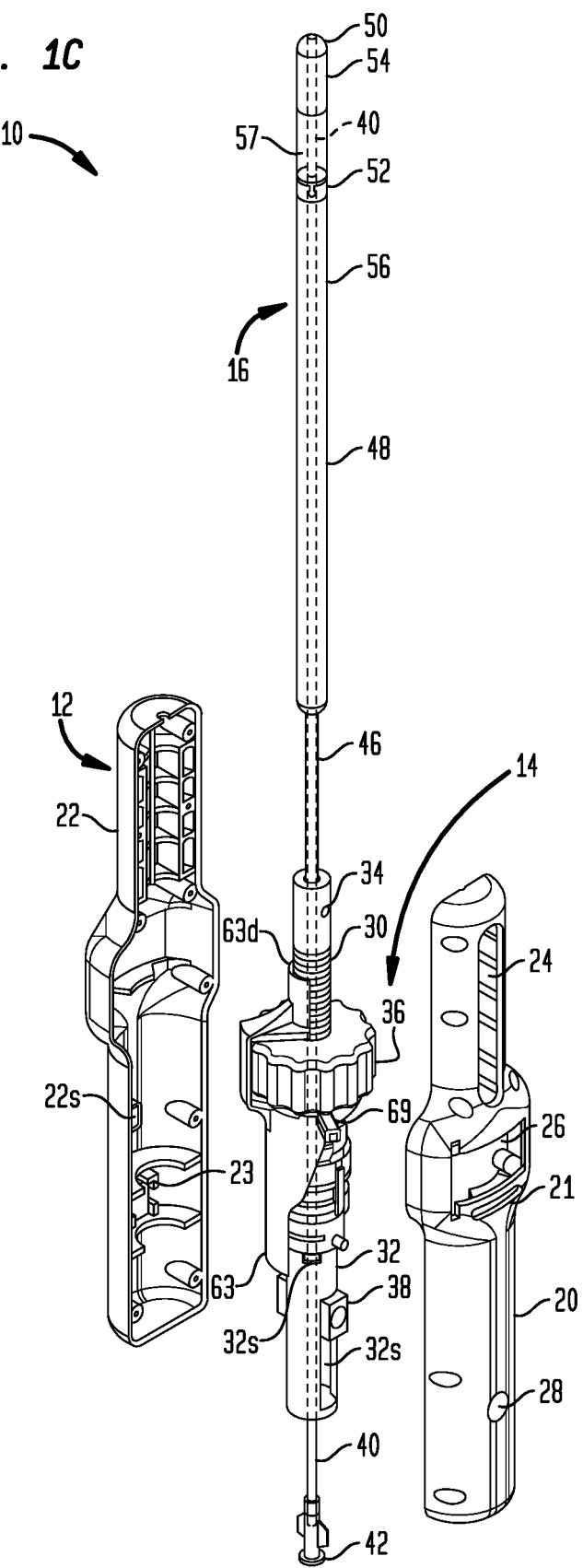

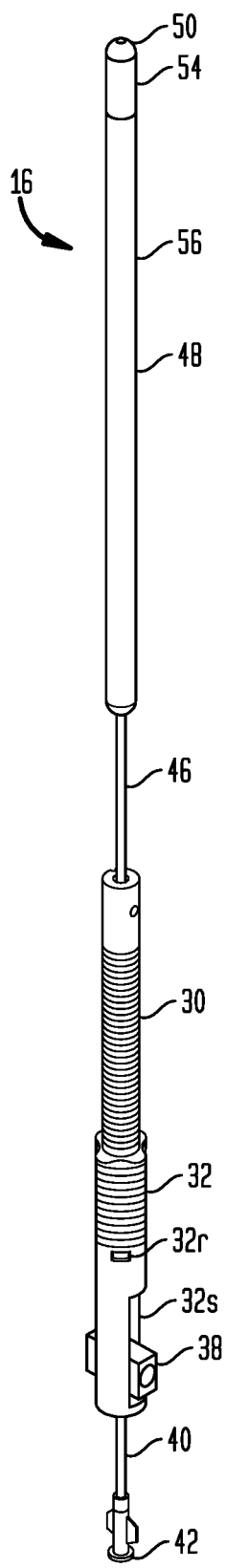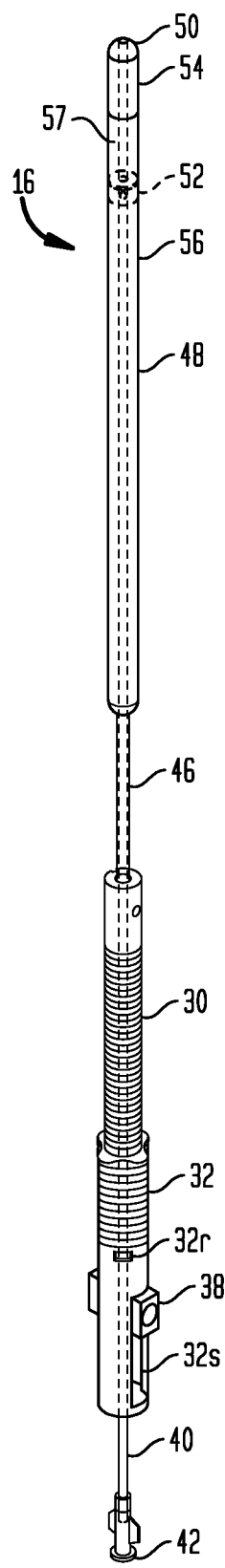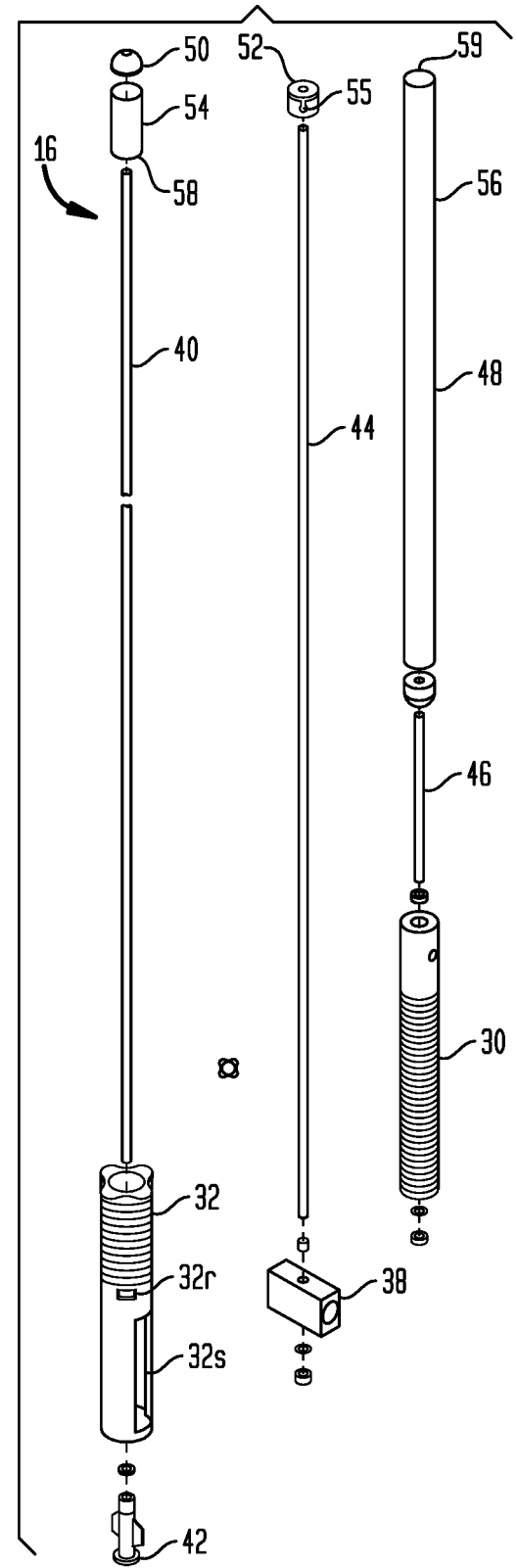

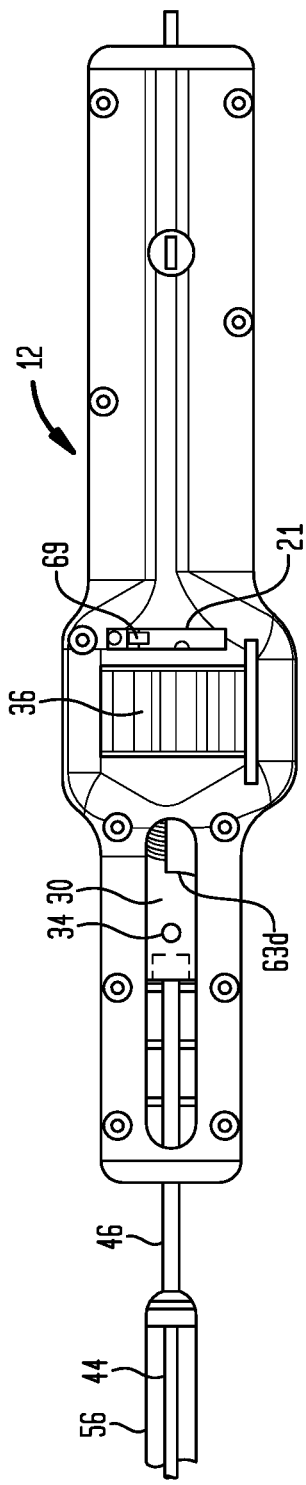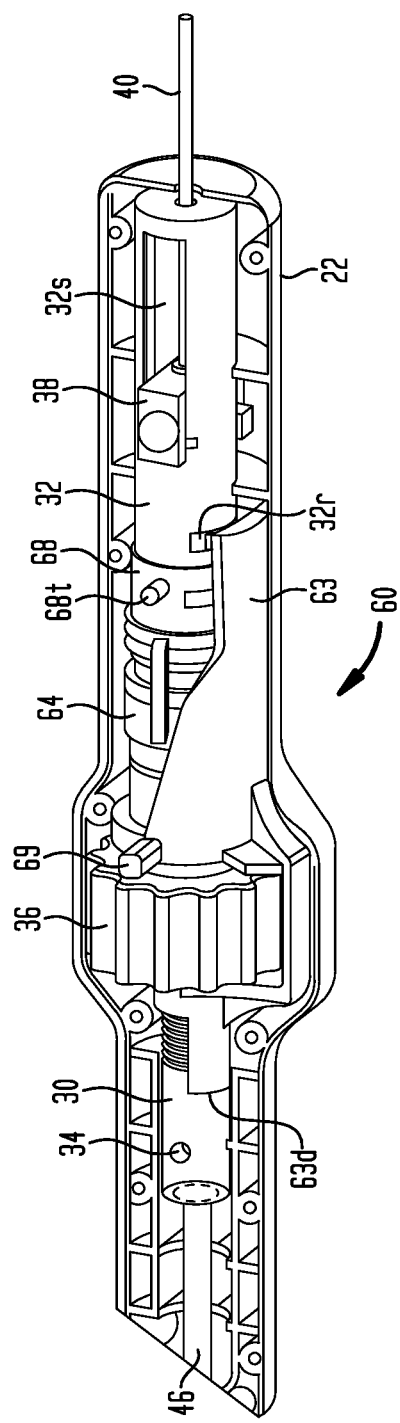

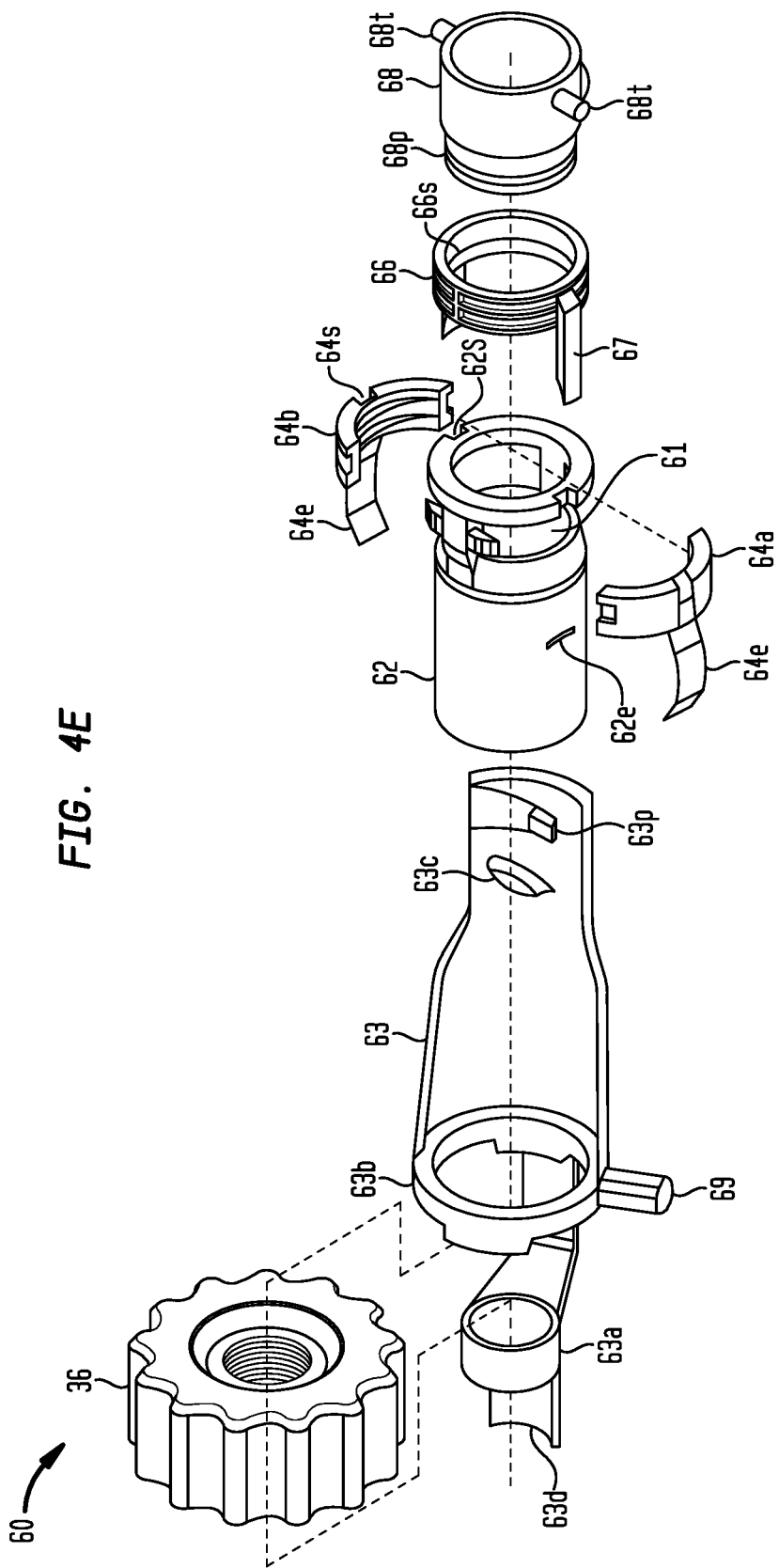

MITRAL VALVE DELIVERY DEVICE

CROSS-REFERENCE TO RELATED APPLICATION

This application is a divisional of U.S. patent application Ser. No. 15/592,737, filed on May 11, 2017, which claims the benefit of the filing date of U.S. Provisional Patent Application No. 62/336,112, filed on May 13, 2016, the disclosures of which are hereby incorporated herein by reference.

BACKGROUND OF THE INVENTION

The present disclosure relates to heart valve replacement and, in particular, to the delivery of collapsible prosthetic heart valves into a patient for implantation. More particularly, the present disclosure relates to devices and methods for delivering and deploying collapsible prosthetic heart valves within native valve annuluses.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

Described herein is a delivery device for a collapsible prosthetic heart valve. The delivery device may include a catheter assembly and an operating handle coupled to the catheter assembly. The catheter assembly may include an inner shaft around which a compartment is defined, and a distal sheath having a proximal segment and a distal segment together configured to enclose the compartment. The operating handle may include a housing defining a movement space therein, a first lead screw fixedly coupled to the proximal segment of the distal sheath and moveable in first and second opposite longitudinal directions within the movement space, a second lead screw coupled to the distal segment of the distal sheath and moveable in the first and second longitudinal directions within the movement space, a knob coupled to the housing and rotatable relative to the housing, the knob being threadedly engaged with the first lead screw, and a coupling assembly. The coupling assembly may have a first condition in which rotation of the knob in one direction moves the first lead screw in the first longitudinal direction and does not move the second lead screw in the first or second longitudinal directions, and a second condition in which rotation of the knob in the one direction simultaneously moves the first lead screw in the first longitudinal direction and the second lead screw in the second longitudinal direction.

Also described herein is an operating handle for a delivery device for a collapsible prosthetic heart valve. The operating handle may include a housing defining a movement space therein, a first lead screw moveable in first and second opposite longitudinal directions within the movement space, a second lead screw moveable in the first and second longitudinal directions within the movement space, a knob coupled to the housing and rotatable relative to the housing, the knob being threadedly engaged with the first lead screw, and a coupling assembly. The coupling assembly may have a first condition in which rotation of the knob in one direction moves the first lead screw in the first longitudinal direction and does not move the second lead screw in the first or second longitudinal directions, and a second condition in which rotation of the knob in the one direction simultaneously moves the first lead screw in the first longitudinal direction and the second lead screw in the second longitudinal direction.

Further described herein is a method of delivering a collapsible prosthetic heart valve in a patient. The method may include providing a delivery device having a catheter assembly and an operating handle. The catheter assembly may include a compartment adapted to receive the valve in an assembled condition and a distal sheath slidable relative to the compartment. The operating handle may include a housing defining a movement space therein and first and second lead screws each movable in first and second opposite longitudinal directions within the movement space. The method may also include loading the valve into the compartment of the catheter assembly and covering the compartment and the valve with proximal and distal segments of the distal sheath, and inserting the catheter assembly into the patient so that the valve is positioned at a target location within the patient. The method may further include partially deploying the valve by moving the first lead screw in the first longitudinal direction within the movement space, and fully deploying the valve by simultaneously continuing movement of the first lead screw in the first longitudinal direction within the movement space and moving the second lead screw in the second longitudinal direction within the movement space.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 1A is a perspective view of a delivery device with an distal sheath being shown as partially transparent and in a partially-retracted position;

FIG. 1B is a perspective view of the delivery device of FIG. 1A with the distal sheath being shown as opaque and in a fully-closed position;

FIG. 1C is a perspective view of the delivery device of FIG. 1A with the handle housing removed;

FIG. 2A is a perspective view of the catheter and threaded rod assemblies of the delivery device of FIG. 1A;

FIG. 2B is a perspective view of the catheter and threaded rod assemblies of FIG. 2A with the sheaths and threaded rods being shown as partially transparent;

FIG. 2C is an exploded perspective view of the catheter and threaded rod assemblies of FIG. 2A;

FIG. 4A is a top view of the operating handle of the delivery device of FIG. 1A;

FIG. 4B is a perspective view of the operating handle of FIG. 4A with a portion of the housing removed;

FIG. 4E is an exploded perspective view of the deployment actuator assembly shown in FIG. 4B;

DETAILED DESCRIPTION

There is a need for further improvements to the devices, systems, and methods for transcatheter delivery and deployment of collapsible prosthetic heart valves, and in particular, self-expanding prosthetic heart valves. Among other advantages, the present invention may address one or more of these needs.

Figure 3A:
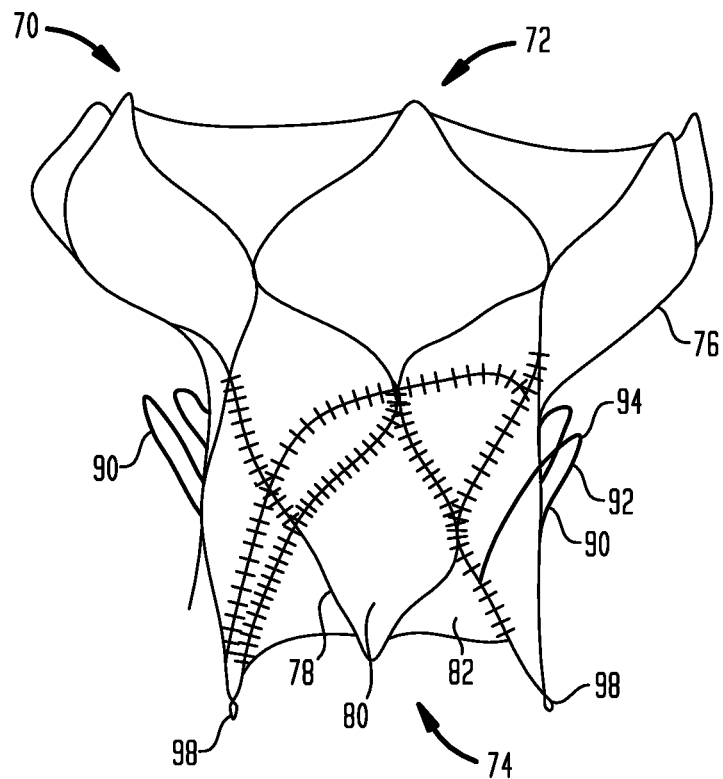
FIG. 3A is a side view of a self-expanding prosthetic heart valve suitable for deployment with the delivery device of FIG. 1A.
Figure 3B:
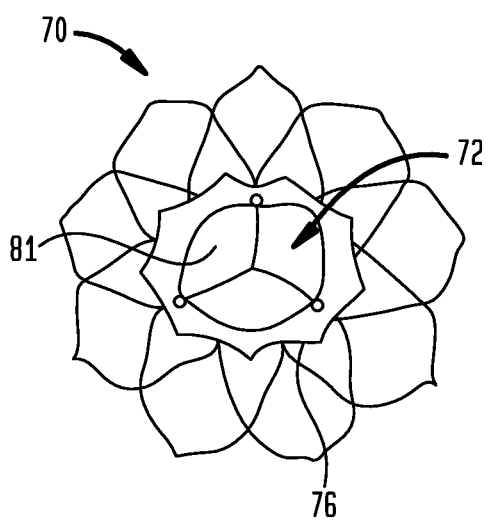
FIG. 3B is a view of the prosthetic heart valve of FIG. 3A from the inlet end.
Figure 3C:
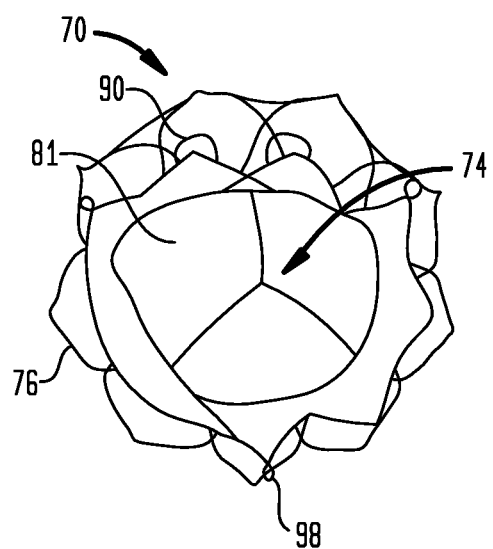
FIG. 3C is a view of the prosthetic heart valve of FIG. 3A from the outlet end.
Figure 3D:
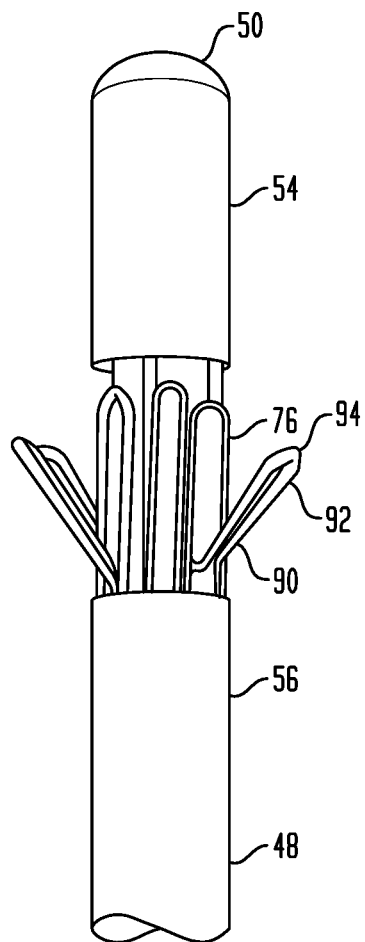
FIG. 3D is a side view of a distal portion of the delivery device of FIG. 1A with a self-expanding stent therein.
Figure 3E:
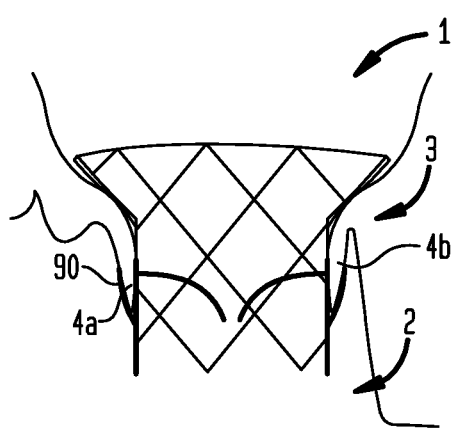
FIG. 3E is a schematic longitudinal cross-sectional view of the prosthetic heart valve of FIG. 3A deployed into a mitral valve annulus of a patient.
Figure 4C:
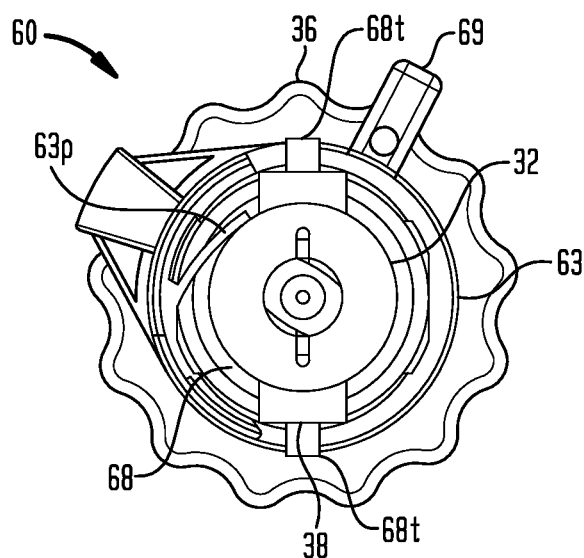
FIG. 4C is an end view of the deployment actuator assembly shown in FIG. 4B.
Figure 4D:
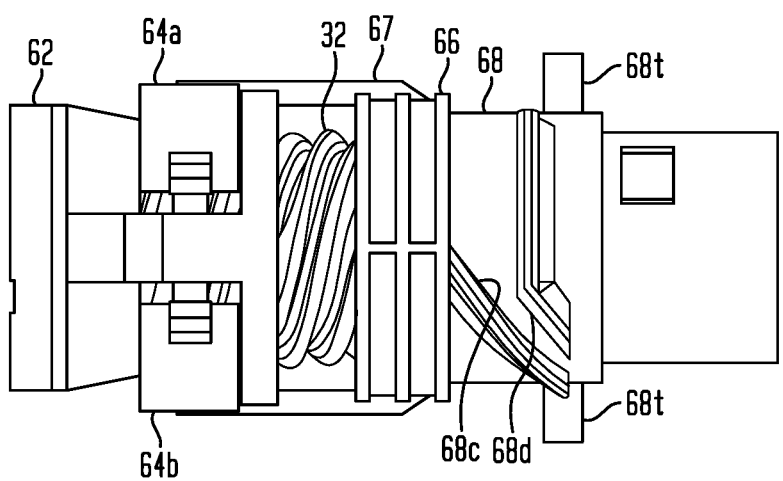
FIG. 4D is an enlarged side view of a portion of the deployment actuator assembly shown in FIG. 4B.

Blood flows through the mitral valve from the left atrium 1 to the left ventricle 2 (FIG. 3E). As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user operating the device in an intended manner "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

Referring now to FIGS. 1A-1C, an exemplary delivery device 10 for use in delivering and deploying a collapsible prosthetic heart valve (or other types of self-expanding collapsible stents) in a patient is shown. Generally, the delivery device 10 includes a handle 12, an actuator 14, and a catheter assembly 16. The catheter assembly 16, which is illustrated as partially transparent in FIG. 1A, may function to deliver the prosthetic heart valve to and deploy the heart valve at a target location. The actuator 14 may function to control deployment of the valve from the catheter assembly 16. The handle 12 may function to facilitate operation of the other components by a user. Each of these components is described in greater detail below. An exemplary method of use of the delivery device 10 and further structural details thereof are shown and described in the co-owned and co-pending U.S. Patent Application Publication No. 2014/0371844, the disclosure of which is hereby incorporated herein by reference.

As illustrated in FIG. 1A, the handle 12 includes a first housing portion 20 and a second housing portion 22. The first and second housing portions 20 and 22 may be individual pieces configured to be joined to one another as shown in FIG. 1A. For example, the housing portions 20 and 22 may include some combination of mating features, such as pegs and corresponding holes, to facilitate connecting the housing portions together. The housing portions 20 and 22 may be connected to one another in any other suitable manner, including, for example, by fasteners, ultrasonic welding, or an adhesive.

The housing portions 20 and 22, individually or collectively, define a number of spaces to house components of the actuator 14 and the catheter assembly 16. For example, the housing portions 20 and 22 define an elongated space in the handle 12 in which an inner lead screw 30 and an outer lead screw 32 are positioned and through which the lead screws may translate. (The inner and outer lead screws 30, 32 may alternatively be referred to in this disclosure as first and second lead screws 30, 32.) The first housing portion 20 may also include an elongated slot 24 oriented in the longitudinal direction of the handle 12 through which a flush port may extend, and a transverse slot 21 through which a lever 69 of a control member 63 may extend. Similarly, the housing portions 20 and 22 may define a generally circular or cylindrical space 26 in which a knob 36 is positioned. Finally, the first housing portion 20 may include a flush aperture 28 sized to receive a flush port on a flush adapter 38 of the catheter assembly 16.

The inner lead screw 30 extends within the elongated space in the handle 12 and into a central bore of the knob 36 sized to receive the inner lead screw. The central bore in the knob 36 may be internally threaded and configured to mate with external threads on the inner lead screw 30. The inner lead screw 30 always remains in threaded engagement with the knob 36. As the knob 36 is longitudinally confined within the space 26, rotation of the knob causes the inner lead screw 30 to translate proximally or distally within the handle 12, depending on the direction of rotation. The inner lead screw 30 may be sized to have a predetermined travel distance within the elongated space of the handle 12, to provide limits to the travel range of the proximal segment 54 of the distal sheath 48, which will be described below. The knob 36 may have a textured cylindrical surface, such as a plurality of spaced ridges, to assist the user in gripping and rotating the knob.

A flush port may be affixed to the inner lead screw 30 at an aperture 34 and may extend within the elongated slot 24. The engagement of the flush port in the elongated slot 24 prevents the inner lead screw 30 from simply rotating with the knob 36 and keeps the inner lead screw aligned in the longitudinal direction of the handle 12. The flush port may further provide limits on the distance that the inner lead screw 30 may translate proximally or distally within the handle 12. The inner lead screw 30 may also include a longitudinal slot in its unthreaded portion configured to slidably engage with a longitudinal rib of the first or second housing portion 20 or 22, which may also prevent the inner lead screw from rotating with the knob.

Figure 6A:
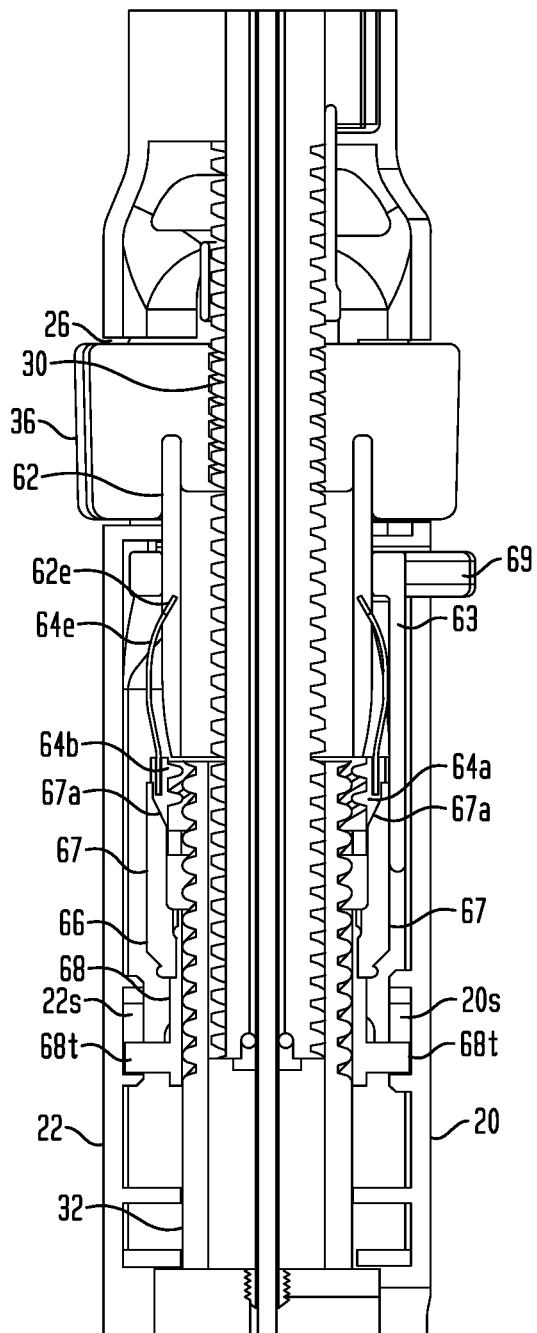
FIG. 6A is an enlarged longitudinal cross-section of the operating handle of FIG. 4A, with the split nut shown disengaged from the threads of the outer threaded rod.
Figure 6B:
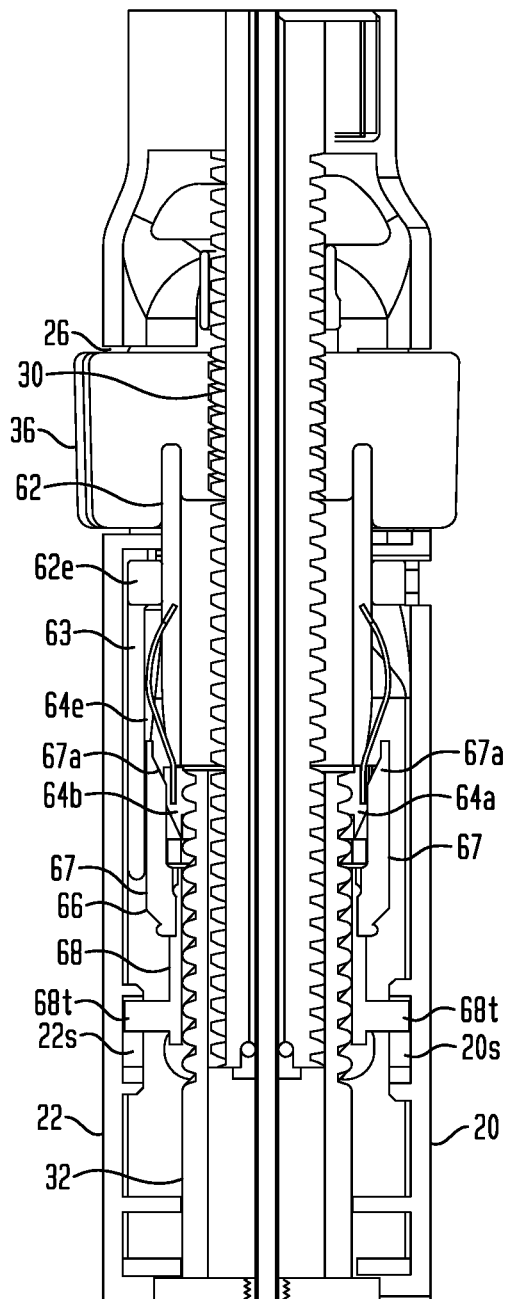
FIG. 6B is an enlarged longitudinal cross-section of the operating handle of FIG. 4A, with the split nut shown in threaded engagement with the outer threaded rod.

The outer lead screw 32 also extends within the elongated space in the handle 12, and it has a longitudinal bore sized to receive the inner lead screw 30. As can be seen in FIGS. 6A and 6B, although the portion of the inner lead screw 30 that extends within the outer lead screw 32 has threads, the longitudinal bore of the outer lead screw is not threaded, so the inner lead screw is freely slidable within the longitudinal bore of the outer lead screw. The outer lead screw 32 includes an elongated slot 32s sized to receive the flush adapter 38. The engagement of the flush adapter 38 with locating tabs 23 in the housing portions 20 and 22 of the handle 12 fixes the location and orientation of the flush adapter and the retaining element 52 (to be described below) relative to the handle, and prevents the outer lead screw from rotating within the handle and keeps the outer lead screw aligned in the longitudinal direction of the handle. The flush adapter 38 may further provide limits on the distance that the outer lead screw 32 may translate proximally or distally within the handle 12, and may provide a limit on the distance that the inner lead screw 30 may translate proximally within the longitudinal bore of the outer lead screw.

An inner shaft 40 of the catheter assembly 16 is also illustrated in FIG. 1A. The inner shaft 40 may extend from beyond a proximal end of the handle 12, through the handle subassembly, to a distal portion of delivery device 10 (the distal portion is described in greater detail below with reference to FIGS. 2A-2C). In particular, the inner shaft 40 may extend from a hub 42 on its proximal end through the inner and outer lead screws 30, 32 and the flush adapter 38, and to the distal portion of the delivery device 10. The hub 42 may be positioned proximally of the proximal end of handle 12 such that, during use, a user may grasp the proximal hub. The hub 42 may be a luer configured to permit flushing of the shaft 40. The inner shaft 40 and the hub 42 may also have an internal lumen configured to receive a guide wire that may extend completely through the delivery system 10 from the hub at the proximal end of the delivery system to a distal tip 50 at the distal end of the delivery system.

FIGS. 2A-2C illustrate additional components of the catheter assembly 16, with the housing portions 20, 22 of the handle 12 removed. In general, the catheter assembly 16 includes the inner shaft 40, described in part above in relation to FIGS. 1A-1C, an inner sheath 44, a middle sheath 46, and an distal sheath 48, shown in FIGS. 1C and 2B as partially transparent. The distal sheath 48 may have a distal segment 54 and a proximal segment 56, described more fully below.

The inner shaft 40 extends from the hub 42 to an atraumatic distal tip 50. The inner shaft 40 is fixedly attached to the hub 42 and the distal tip 50, and the distal tip is fixedly attached to the distal segment 54. The inner shaft 40 is removably attached to the outer lead screw 32 via mating threads, so that the user may disengage the outer lead screw from the inner shaft and may selectively push or pull the hub 42 distally or proximally, as will be described in greater detail below. When the inner shaft 40 is attached to the outer lead screw 32, proximal or distal translation of the outer lead screw causes corresponding translation of the inner shaft as well as the distal segment 54 of the distal sheath to which the inner shaft is connected.

The inner sheath 44 is positioned over the inner shaft 40 and extends from the flush adapter 38, through the knob 36 and the inner and outer lead screws 30, 32, and terminates at a retaining element 52. The inner sheath 44 is fixedly attached to the flush adapter 38 and the retaining element 52. The location and orientation of the inner sheath 44 are fixed with respect to the handle 12 due, at least in part, to its connection to the flush adapter 38, which is held in a fixed position by locating tabs 23 in the housing portions 20 and 22 of the handle 12.

The middle sheath 46 is positioned over the inner sheath 44 and the inner shaft 40, and extends from the distal end of the inner lead screw 30 to the proximal end of the distal sheath 48. The middle sheath 46 is fixedly attached to both the inner lead screw 30 and the proximal end of the distal sheath 48 such that proximal or distal translation of the inner lead screw causes corresponding translation of the middle sheath as well as the segment of the distal sheath to which the middle sheath is connected.

The distal sheath 48 is positioned over the inner sheath 44 and the inner shaft 40, and extends from the distal end of the middle sheath 46 to the atraumatic distal tip 50. The distal tip 50 may be blunt to facilitate advancement of the delivery device 10 without injury to the patient's tissue. For example, the distal tip 50 may have a rounded distal surface that faces away from the longitudinal axis of the distal sheath 48. The distal sheath 48 may have a distal segment 54 and a proximal segment 56. The distal segment 54 may be coupled to the distal tip 50 so that movement of the inner shaft 40 (for example, by a user rotating the knob 36) results in a corresponding movement of the distal segment. The proximal segment 56 may be coupled to the middle sheath 46, which in turn is coupled to the lead screw 30, so that movement of the middle sheath (for example, by a user rotating the knob 36) results in a corresponding movement of the proximal segment. In some embodiments, the distal tip 50 and/or the distal segment 54 of the distal sheath 48 may be made of material that limits reflection under echocardiographic imaging.

The distal segment 54 and the proximal segment 56 may include complementary releasable coupling features such as ribs, clips or fasteners for ensuring that they do not become separated from one another during delivery of a prosthetic valve into a patient. In one example, the proximal end 58 of the distal segment 54 may be slightly smaller in diameter than the distal end 59 of the proximal segment 56 such that these ends may mate with one another in an overlapping friction fit relationship. In the embodiment shown in the figures, the engagement of the flexible arm 63p in a corresponding recess 32r in the outer lead screw 32 may accomplish the function of avoiding accidental separation of the distal segment 54 and the proximal segment 56 until such separation is desired.

The space between the retaining element 52 and the distal tip 50 defines a compartment 57 for housing a prosthetic heart valve. Specifically, a prosthetic heart valve may be disposed about the inner shaft 40 in the compartment 57 and covered by the distal sheath 48. The retaining element 52 may include a plurality of recesses 55 distributed circumferentially around its perimeter, the recesses being configured to accept retainers disposed near the outflow end of the prosthetic heart valve, as will be described in more detail below. The distal segment 54 and the proximal segment 56 of the distal sheath 48 may be translatable relative to one another to form an increasing gap G therebetween (FIG. 1A) so as to expose the prosthetic heart valve in the compartment 57 for deployment. Further description of the aforementioned structural details of the delivery device 10 is provided in the co-owned and co-pending U.S. Patent Application Publication No. 2014/0371844.

The proximal and distal translation of the distal segment 54 and the proximal segment 56 of the distal sheath 48 to deploy a prosthetic heart valve can be controlled by one-handed operation of the handle 12 by a user. The knob 36 is always in threaded engagement with the inner lead screw 30, which is coupled to the proximal segment 56 via the middle sheath 46. The knob 36 can be selectively coupled with the outer lead screw 32 when a user moves a lever 69 of a control member 63 that will be described below. The outer lead screw 32 is coupled to the distal segment 54 via the inner shaft 40. When the knob 36 is coupled with both the inner and outer lead screws, rotation of the knob by a user will translate both the distal segment 54 and the proximal segment 56 in opposite longitudinal directions.

The threads of the inner and outer lead screws 30, 32 are shown in the figures as being oriented in opposite directions from one another, with the pitch of the outer lead screw threads being greater than the pitch of the inner lead screw threads. This can be seen in FIGS. 2A, 2B, and 5A-5C. In this embodiment, a single complete rotation of the knob 36 by the user will move the outer lead screw 32 a greater longitudinal distance than the inner lead screw 30, and in the opposite direction. In other embodiments, the thread pitch of the inner and outer lead screws 30, 32 may be closer to one another so that they travel similar distances upon rotation of the knob 36, or the pitch of the inner screw may be greater than the pitch of the outer screw to accommodate alternative designs of the collapsible prosthetic heart valve 70 or other implantable medical device to be deployed into a patient.

FIGS. 3A-3C show a collapsible prosthetic heart valve 70 in an expanded condition after being released from the compartment 57 of the delivery device 10 by the distal movement of the distal segment 54 of the distal sheath 48 relative to the prosthetic heart valve and/or the proximal movement of the proximal segment 56 of the distal sheath relative to the prosthetic heart valve.

The collapsible prosthetic heart valve 70 is designed to replace the function of the native mitral valve of a patient. The prosthetic heart valve 70 has an inflow end 72 and an outflow end 74. The prosthetic heart valve 70 may be generally cylindrically shaped in the expanded condition and may include features for anchoring to native heart tissue, as will be discussed in more detail below. Throughout this disclosure, a prosthetic mitral valve is used as an exemplary valve to be loaded into a delivery device such as the delivery device 10. However, the delivery device 10 described herein may be used to deliver other collapsible valves, e.g., a collapsible prosthetic aortic valve, other collapsible stents, or other collapsible medical devices.

The prosthetic heart valve 70 may include a stent 76, which may be formed from biocompatible materials that are capable of self-expansion, such as, for example, shape-memory alloys including Nitinol. The stent 76 may include a plurality of struts 78 that form closed cells 80 connected to one another in one or more annular rows around the stent. The cells 80 may all be of substantially the same size around the perimeter and along the length of the stent 76. Alternatively, the cells 80 near the inflow end 72 of the prosthetic valve 70 may be larger or smaller than the cells near the outflow end 74 of the valve. The stent 76 may be expandable to provide a radial force to assist with positioning and stabilizing the prosthetic heart valve 70 within the native mitral valve annulus of a patient.

The prosthetic heart valve 70 may also include a valve assembly disposed within the stent 76. The valve assembly may include a plurality of leaflets 81 attached to a cylindrical cuff 82. The leaflets may replace the function of the native mitral valve leaflets of the patient. That is, the leaflets coapt with one another to function as a one-way valve. The prosthetic heart valve 70 may have two or more leaflets when used to replace the mitral valve or other cardiac valves within a patient. The valve assembly of the prosthetic heart valve 70 may be substantially cylindrical in the expanded condition. Both the cuff 82 and the leaflets 81 may be wholly or partly formed of any suitable biological material, such as bovine or porcine pericardium, or polymers, such as polytetrafluoroethylene (PTFE), urethanes and the like. The valve assembly may be secured within the interior of the stent 76 by suturing to the struts 78 or by using tissue glue, ultrasonic welding, or other suitable attachment methods.

Referring to FIGS. 3D and 3E, the prosthetic heart valve 70 includes additional securement features in the form of anchor arms 90 that hook under native mitral valve leaflets 4a, 4b to help prevent the prosthetic heart valve from migrating into the left atrium 1. The anchor arms 90 may each be formed of a single wire 92 bent or otherwise formed into a body portion. The wire 92 is preferably a shape-memory alloy such as Nitinol, so that when the prosthetic heart valve 70 is deployed from the delivery device 10, the stent 76 automatically radially expands to the shape shown in FIG. 3A, and tips 94 of the anchor arms 90 automatically extend away from the stent 76. In one example, the wire 92 is formed of Nitinol having a diameter of about 0.015 inches (0.38 mm). In the example shown in FIG. 3A, each anchor arm 90 is formed of a looped or bent wire 92 having a rounded or blunted central tip 94. In other embodiments, each anchor arm may be formed of a single wire extending to a free tip, or other configurations and/or shapes of anchor arms may be used.

Each anchor arm 90 may extend away from the struts 78 so that the tip 94 of the wire 92 lies at a spaced distance radially outward from the struts 78. Preferably, the tip 94 of each wire 92 is blunt and/or rounded to reduce the likelihood of the tips damaging the native tissue hooked by the anchor arms 90. In addition or alternatively, a blunted and/or rounded end cap may be assembled over or onto the tips 94 of the wires 92 and fixed to the tips, for example by welding, to provide an atraumatic tissue contact surface. Other exemplary types of self-expanding prosthetic heart valves 70 and further structural details thereof are shown and described in the co-owned and co-pending U.S. patent application Ser. No. 15/077,070, filed Mar. 22, 2016, the disclosure of which is hereby incorporated herein by reference.

The prosthetic heart valve 70 may also include a number of retainers 98 extending from the outflow end 74 of the stent 76. Among other things, the retention of the retainers 98 in the recesses 55 (FIG. 2C) of the retaining element 52 prevents the outflow end 74 of the prosthetic heart valve 70 from being inadvertently or unintentionally deployed from the proximal segment 56 of the distal sheath 48. The retention of the retainers 98 in the recesses 55 of the retaining element 52 also serves to fix the rotational orientation of the prosthetic heart valve 70 relative to the handle 12. In one example, the retaining element 52 is configured to receive the prosthetic heart valve 70 in an orientation having an anterior side of the valve facing upward relative to the handle 12, in which the upward direction is a direction from the second housing portion 22 towards the first housing portion 20. During the deployment of the prosthetic heart valve 70 from the compartment 57, a user may rotate the knob 36 in a first direction, thereby moving the inner lead screw 30, the middle sheath 46, and the proximal segment 56 of the distal sheath 48 in a proximal direction. This proximal movement of the proximal segment 56 relative to the prosthetic heart valve 70 exposes the retainers 98 and allows them to disengage from the recesses 55 of the retaining element 52. Once disengaged from the retaining element 52, the prosthetic heart valve 70 may fully deploy into the patient.

FIGS. 4A-4E illustrate the components of the deployment actuator assembly located within the handle 12. The prosthetic heart valve 70 can be deployed from the compartment 57 by a user operating the handle 12 with a single hand. Through the use of a coupling assembly 60, the knob 36 can be rotated to move only the proximal segment 56 of the distal sheath (while the distal segment 54 remains stationary), or the knob can be rotated to simultaneously move both the proximal and distal segments of the distal sheath.

The coupling assembly 60 is configured to permit a split nut 64 to be selectively placed in threaded engagement with the outer lead screw 32. The split nut has first and second nut portions 64a and 64b that are internally threaded to mate with the threads of the outer lead screw 32. The split nut 64 is constrained from longitudinal movement by being movably mounted within openings 61 near the proximal end of a coupling cylinder 62 that is fixedly attached to the knob 36 at the distal end of the coupling cylinder. The first and second nut portions 64a and 64b have freedom of motion to slide in a substantially perpendicular direction towards or away from the outer lead screw 32, but they are constrained from longitudinal movement relative to the housing portions 20, 22 of the handle 12 by the coupling cylinder 62.

A nut ramp 66 may be mounted around the outer lead screw 32 adjacent the coupling cylinder 62. The nut ramp 66 has an annular body with a pair of cam arms 67 projecting distally therefrom and slidably positioned within corresponding slots 64s in respective nut portions 64a and 64b, as well as corresponding slots 62s in the coupling cylinder 62. The engagement of the cam arms 67 in the slots 62s and 64s rotationally fixes the nut ramp 66 and the split nut 64 to the coupling cylinder 62. The cam arms 67 each have a cam surface 67a (FIGS. 6A and 6B) that is angled relative to the longitudinal axis of the handle 12. The cam arms 67 are adapted to translate movement of the nut ramp 66 distally along the longitudinal axis into lateral movement of the first and second nut portions 64a and 64b towards and into threaded engagement with the outer lead screw 32. In that regard, the annular body of the nut ramp 66 is sized so that the nut ramp is freely slidable over the outer lead screw 32 without engaging the threads of same.

When the cam arms 67 are not forcing the first and second nut portions 64a and 64b into threaded engagement with the outer lead screw 32, the bias of leaf springs 64e (FIG. 4E) pull the first and second nut portions laterally away from the outer lead screw. The leaf springs 64e each have a first end captured in a slot 62e in the coupling cylinder 62 and a second end captured in a corresponding slot in the first and second nut portions 64a and 64b, respectively (also visible in FIGS. 6A and 6B). Although leaf springs 64e are shown in the figures, in other embodiments, other types of springs or energy storage mechanisms (e.g., coil springs, elastic bands, living hinges, etc.) may be used in place of the leaf springs to pull the first and second nut portions 64a and 64b away from the outer lead screw 32 when the nut ramp is moved proximally along the longitudinal axis.

A ring 68 may be mounted around the outer lead screw 32 adjacent the nut ramp 66. The distal end of the ring 68 may be snap fit into the nut ramp 66 by engagement of an annular protrusion 68p on the ring into a corresponding annular slot 66s in the inward-facing annular surface of the nut ramp. The ring 68 has an annular body and a pair of diametrically opposed bosses 68t projecting radially therefrom. The bosses 68t are positioned within corresponding slots 20s and 22s (FIGS. 6A and 6B) formed longitudinally in the respective housing portions 20, 22 of the handle 12. The engagement of the bosses 68t in the slots 20s and 22s permits the ring 68 to translate distally and proximally within a predetermined distance within the handle 12, but prevents the ring from rotating.

A control member 63 may be mounted around the inner lead screw 30. The control member may have a distal ring 63a extending around the inner lead screw 30 distally of the knob 36 and a proximal ring 63b extending around the inner lead screw proximally of the knob. The knob 36 may be mounted coaxially with and between the distal and proximal rings 63a, 63b, so that the control member 63 is constrained from longitudinal movement relative to the housing portions 20, 22 of the handle 12 by the knob, but the control member and the knob may rotate about the longitudinal axis relative to one another. The control member 63 includes a lever 69 that projects through a transverse slot 21 in the first housing portion 20 of the handle 12, where it is available to be moved by the user. Sliding the lever 69 laterally within the slot 21 rotates the control member 63 about the inner and outer lead screws 30, 32.

The lever 69 may have a first position adjacent a first end of the slot 21, a second position adjacent a second opposite end of the slot, and an intermediate position near the middle of the slot, as will be described more fully below with reference to operation of the delivery device 10. In one embodiment, a sidewall of the first housing portion 20 within the slot 21 may include three detents near the first and second ends of the slot and near the middle of the slot, respectively. The lever 69 may include a rounded bump on a sidewall thereof facing the sidewall within the slot, the rounded bump being configured to locate in one of the detents when the lever moves to the corresponding first, second, or intermediate position. Such a bump and detent feature of the slot 21 and the lever 69 may make it easier for a user to maintain the lever at the first, second, and intermediate positions during loading and/or deployment of a prosthetic heart valve 70.

The control member 63 includes a distal end 63d that extends partially around the inner lead screw 30 and is adapted to interfere with a flush port that may be affixed to the inner lead screw at the aperture 34 when the lever 69 is in the first position shown in FIG. 4A, thereby preventing the inner lead screw from proximal movement beyond a certain position. When the lever 69 has been moved away from the first position as shown in FIG. 4B, the distal end 63d no longer interferes with the longitudinal travel path of the flush port, so the inner lead screw 30 is not prevented from continued proximal movement.

The selective interference between the control member 63 and the flush port affixed to the inner lead screw 30 may function as a resheathing lock adapted to temporarily limit the proximal movement of the proximal segment 56 of the distal sheath 48. This limitation on the proximal movement of the proximal segment 56 will ensure that the retainers 98 of the prosthetic valve 70 remain captured by the retaining element 52 while the anchor arms 90 are released from the proximal segment, thereby preventing the user from completing the deployment of the prosthetic valve 70 when unintended. The initial distance that the proximal segment 56 of the distal sheath 48 can travel before being limited by the control member 63 may depend on the structure of the particular prosthetic valve to be deployed. In the example shown in the figures, the initial travel distance of the proximal segment 56 is about 14 mm less than the amount of travel needed to expose the retainers 98 of the prosthetic valve 70.

Figure 5A:
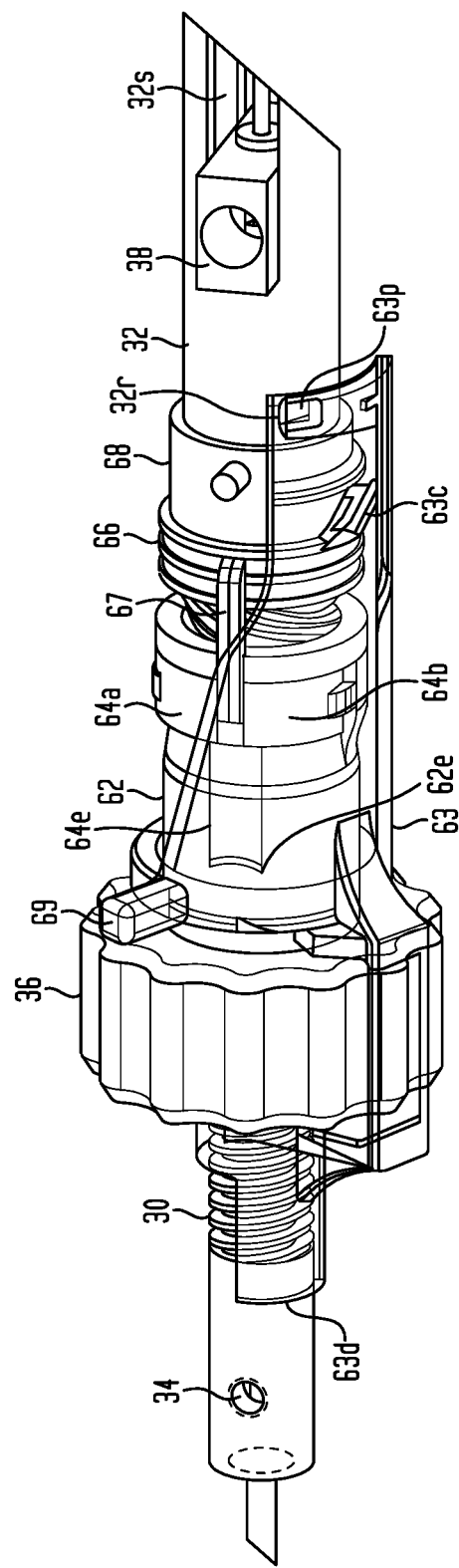
FIG. 5A is a partially transparent side perspective view of a portion of the deployment actuator assembly shown in FIG. 4B, with the nut ramp in a proximal position.
Figure 5B:
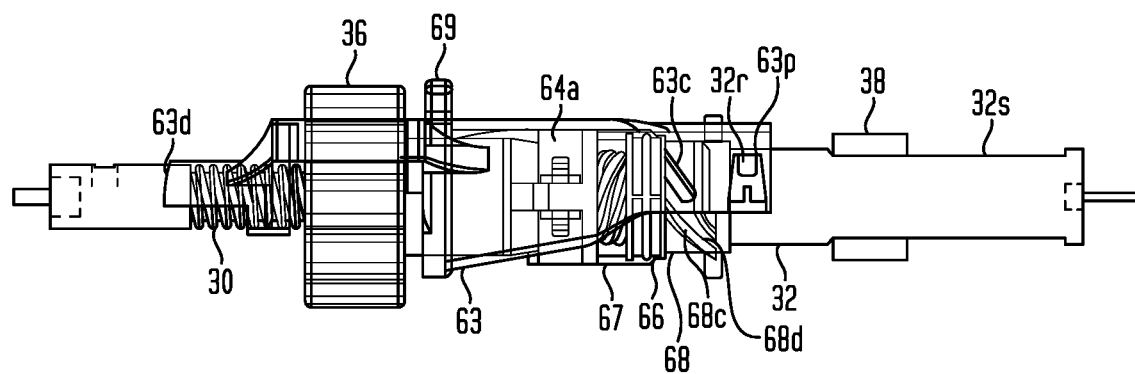
FIG. 5B is a partially transparent side view of the portion of the deployment actuator assembly shown in FIG. 5A.
Figure 5C:
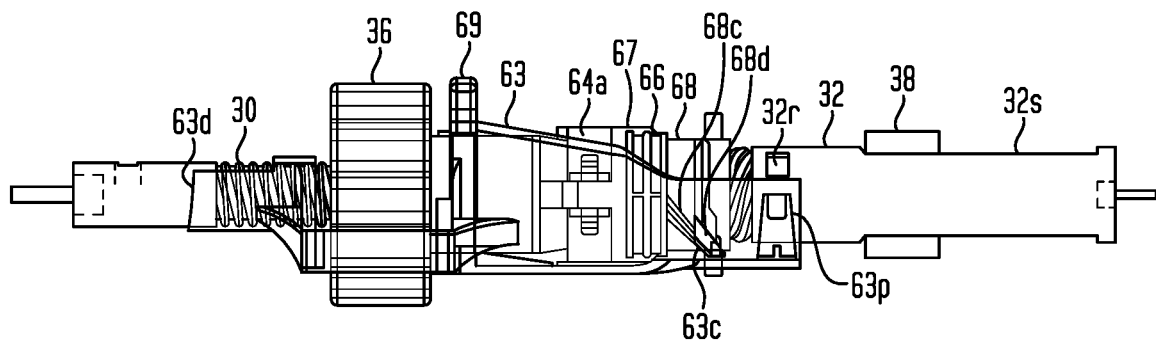
FIG. 5C is partially transparent a side view of the portion of the deployment actuator assembly shown in FIG. 5A, with the nut ramp in a distal position.

Referring to FIGS. 5A-5C, the control member 63 further includes a cam element 63c and a flexible arm 63p that each project laterally inward from a body of the control member towards the outer lead screw 32. The cam element 63c is adapted to contact cam surfaces 68c and 68d (best seen in FIG. 4D) that extend laterally from the body of the ring 68 away from the outer lead screw 32 at an angle relative to the longitudinal axis of the handle 12. The flexible arm 63p is adapted to engage a corresponding recess 32r in the outer lead screw 32.

When engaged with the cam surfaces 68c and/or 68d, the cam element 63c is adapted to translate rotational movement of the control member 63 about the longitudinal axis into distal or proximal movement of the ring 68 and the nut ramp 66 along the longitudinal axis relative to the handle 12. As described above, distal movement of the nut ramp 66 along the longitudinal axis causes lateral movement of the first and second nut portions 64a and 64b towards the outer lead screw 32, while proximal movement of the nut ramp 66 along the longitudinal axis causes lateral movement of the first and second nut portions away from the outer lead screw through the biasing action of the leaf springs 64e. Thus, rotation of the control member 63 about the longitudinal axis can cause the split nut 64 to be selectively placed in threaded engagement with the outer lead screw 32 or disengaged from the outer lead screw. In other embodiments, the angles and positions of the cam surfaces 68c and/or 68d may be modified to alter the amount of rotation of the lever 69 that is required to engage or disengage the nut portions 64a, 64b from the outer lead screw 32. Depending on the position of the lever 69, the flexible arm 63p is adapted to selectively prevent or permit distal or proximal movement of the outer lead screw 32 along the longitudinal axis of the handle 12. When the flexible arm 63p is engaged in the recess 32, distal or proximal movement of the outer lead screw 32 is prevented, which may prevent inadvertent actuation of the distal segment 54 of the distal sheath 48 when unintended.

When the lever 69 is in the first position shown in FIGS. 5A, 5B, and 6A, the nut ramp 66 is in a proximal position with its annular body spaced apart from the proximal end of the coupling cylinder 62, the first and second nut portions 64a and 64b are disengaged from the outer lead screw 32, and the flexible arm 63p is engaged in the recess 32r, thereby preventing distal or proximal movement of the outer lead screw. As a user slides the lever 69 to a second position, the control member 63 is rotated about the outer lead screw 32 to the position shown in FIG. 5C. This rotation of the control member 63 moves the cam element 63c into contact with the cam surface 68c on the ring 68 and withdraws the flexible arm 63p out of the recess 32r, thereby freeing the outer lead screw 32 for proximal or distal movement. As the cam element 63c slides along the cam surface 68c, the ring 68 and the nut ramp 66 connected thereto are forced to move distally along the outer lead screw 32, and the cam arms 67 of the nut ramp contact the nut portions 64a and 64b and force them radially inward into threaded engagement with the outer lead screw. This inward movement of the nut portions 64a and 64b flexes the leaf springs 64e against their bias, thereby storing energy. The threaded engagement of the nut portions 64a and 64b with the outer lead screw 32 causes the distal segment 54 of the distal sheath 48 to move distally as the knob 36 is rotated in the first direction (the same direction that causes the proximal segment 56 of the distal sheath to move proximally).

Sliding the lever 69 back to the first position causes the control member 63 to rotate in the opposite direction to the position shown in FIG. 5B. This rotation of the control member 63 forces the cam element 63c into contact with the cam surface 68d on the ring 68. As the cam element 63c slides along the cam surface 68d, the ring 68 and the nut ramp 66 connected thereto are forced to move proximally along the outer lead screw 32, pulling the cam arms 67 off of the nut portions 64a and 64b. The biasing force of the leaf springs 64e then pull the nut portions 64a and 64b out of engagement with the outer lead screw 32. As the lever 69 reaches the first position, the flexible arm 63p flexes back into engagement with the recess 32r, thereby preventing distal or proximal movement of the outer lead screw 32. The flexible arm 63p and the recess 32r are configured such that the flexible arm only engages in the recess when the outer lead screw 32 is in its proximalmost position relative to the handle.

The operation of the delivery device 10 to deploy the prosthetic heart valve 70 will now be described. In a typical procedure to deploy the prosthetic heart valve 70 into a patient, the valve may be inserted using a transapical approach, as would readily be known to one having ordinary skill in the art. Briefly, the user would insert the distal end of the delivery device 10 through an intercostal space between the patient's ribs and into the apex of the patient's heart, and through the left ventricle to the mitral valve annulus, where the prosthetic heart valve 70 would be deployed. Echocardiographic imaging, e.g., intracardiac echocardiography (ICE), transesophageal echocardiography (TEE), or transthoracic echocardiography (TTE), may be used to visualize the position of the distal end of the delivery device 10 during deployment of the valve 70.

To load the delivery device 10 with a collapsible prosthetic valve the user may place the lever 69 of the control member 63 in an intermediate position near the middle of the slot 21, which can be seen in FIG. 4B. In this position, the distal end 63d of the control member 63 is not in the path of the flush port that may be affixed to the inner lead screw 30 at the aperture 34, so the proximal segment 56 of the distal sheath 48 can be moved to its proximalmost position to expose the retaining element 52 by rotating the knob 36 in the first direction. Also in this position, the flexible arm 63p of the control member 63 is not engaged with the recess 32r of the outer lead screw 32, and the ring 68 is in its proximalmost position, so the nut portions 64a and 64b are not engaged with the outer lead screw. The outer lead screw 32 can be manually pushed to its distalmost position by a user grasping and pushing the hub 42 distally, which will move the distal segment 54 of the distal sheath 48 to its distalmost position. This will expose the maximum amount of the compartment 57 for compressing and loading of the prosthetic valve 70, which may be accomplished, for example, using the mitral valve loading tool shown and described in the co-owned and co-pending U.S. patent application Ser. No. 15/072,728, filed Mar. 17, 2016, the disclosure of which is hereby incorporated herein by reference. Alternatively, the outer lead screw 32 may be moved to its distalmost position for valve loading by rotation of the knob 36 with the lever 69 in the first position near a first end of the slot 21.

To cover the compartment 57 with the distal sheath 48 to hold the prosthetic valve 70 in the compressed state, the distal segment 54 of the distal sheath 48 may be moved to its proximalmost position by a user grasping and pulling the hub 42 proximally. The knob 36 may then be rotated in a second direction opposite the first direction, which will move the proximal segment 56 of the distal sheath distally until the distal end 59 of the proximal segment 56 contacts the proximal end 58 of the distal segment 54. The fully closed compartment 57 is shown in FIG. 1B, for example. Alternatively, the knob 36 may be rotated in a second direction opposite the first direction to move the proximal segment 56 of the distal sheath 48 to its distalmost position to completely cover the valve 70, the distal segment 54 of the may be moved proximally to contact the proximal segment by a user grasping and pulling the hub 42 proximally, and then the knob may be rotated in the first direction simultaneously with pulling the hub proximally to slide the distal segment over a portion of the valve (the arterial section of the valve), while leaving the anchor arms 90 (the ventricular section of the valve) within the proximal segment.

To use the operating handle 12 to deploy a prosthetic valve 70 that has been loaded into the compartment 57 and covered by the distal sheath 48, the user may move the lever 69 of the control member 63 to the first position near a first end of the slot 21, which can be seen in FIG. 4A. In this position, the distal end 63d of the control member 63 is positioned in the path of the flush port that may project from the inner lead screw 30 into the longitudinal slot 24. Therefore, in this first position of the lever 69, the proximal segment 56 of the distal sheath 48 will be permitted to move proximally, but not to its proximalmost position. Also in this position of the lever 69, the flexible arm 63p of the control member 63 is engaged with the recess 32r of the outer lead screw 32 (when the outer lead screw is in its initial proximalmost position relative to the handle 12), thereby fixing the position of the outer lead screw relative to the handle, and the ring 68 and the nut ramp 66 are in their proximalmost positions, so the nut portions 64a and 64b are not engaged with the outer lead screw.

At this point, the user may insert the distal end of the delivery device 10 into a patient, and the compartment 57 may be maneuvered to the target location, such as the native mitral annulus of the patient. To begin uncovering the prosthetic heart valve 70, the user may rotate the knob 36 in the first direction, which will move the inner lead screw 30 and the proximal segment 56 of the distal sheath 48 proximally. The user may continue moving the proximal segment 56 proximally until the anchor arms 90 of the prosthetic heart valve 70 extend laterally away from the stent 76 and are positioned around the native mitral valve leaflets (e.g., as shown in FIG. 3E).

Once the user is satisfied with the position of the anchor arms 90, the user may fully deploy the prosthetic heart valve 70. To do so, the user moves the lever 69 of the control member 63 to the second position near a second end of the slot 21, as shown in FIGS. 1B and 5C. In this position of the lever 69, the distal end 63d of the control member 63 is no longer in the path of the flush port, the flexible arm 63p of the control member 63 is not engaged with the recess 32r of the outer lead screw 32, and the ring 68 and the nut ramp 66 are in their distalmost positions so that the nut portions 64a and 64b are engaged with the outer lead screw. At this point, the user may continue to rotate the knob 36 in the first direction, which will simultaneously move the inner lead screw 30 and the proximal segment 56 in the proximal direction and the outer lead screw 32 and the distal segment 54 in the distal direction until the prosthetic heart valve 70 completely expands and separates from the delivery device 10. (In other embodiments, the pitches of the lead screws 30 and 32 may be adjusted to alter the timing of the movement of the distal and proximal segments 54, 56. In some examples, rotation of the knob 36 when the lever 69 is in the second position may not simultaneously move both of the lead screws 30, 32.)

Next, the user may re-close the compartment 57 so that the proximal end 58 of the distal segment 54 will contact the distal end 59 of the proximal segment 56, thereby minimizing the risk that tissue of the patient becomes snagged on the distal segment 54 during withdrawal of the catheter assembly 16 from the patient. To re-close the compartment, the user may grasp and rotate the hub 42 relative to the handle 12 to unscrew the inner shaft 40 from the outer lead screw 32. (In other embodiments, the inner shaft 40 may be decoupled from the outer lead screw 32 via alternative mechanisms, such as a quick release lever, button, or the like.) Once the inner shaft 40 is decoupled from the outer lead screw 32, the user may pull the hub 42 proximally relative to the handle to freely slide the inner shaft proximally until the distal segment 54 contacts the proximal segment 56. Although the proximal segment 56 will be is in its proximalmost position after deployment of the prosthetic heart valve 70, the inner shaft 40 can be pulled proximally by a sufficient distance to permit the distal segment 54 to contact the proximal segment, thereby closing the compartment 57. Once the compartment 57 is closed, the catheter assembly 16 may be withdrawn from the patient.

If, at any point during valve deployment, the user desires to resheathe the valve 70 while the valve is partially deployed, to either reposition the valve or withdraw the valve from the patient, the user may rotate the knob 36 in the second direction to move the proximal segment 56 of the distal sheath 48 to its distalmost position to completely cover the valve 70. The distal segment 54 of the may be moved proximally to contact the proximal segment 56 by a user grasping and pulling the hub 42 proximally. Then, the delivery device 10 may be withdrawn from the patient, or the valve 70 may be repositioned within the distal sheath 48 by rotating the knob 36 in the first direction simultaneously with pulling the hub proximally to slide the distal segment over a portion of the valve (the arterial section of the valve), while leaving the anchor arms 90 (the ventricular section of the valve) within the proximal segment. The distal end of the delivery device 10 may then be repositioned within the native mitral valve annulus, and deployment of the valve may be reattempted.

Although in the embodiments shown herein, a threaded knob 36 is configured to mate with an inner lead screw 30 to move a proximal segment 54 of a distal sheath 48, the invention contemplates other coupling mechanisms. For example, in other embodiments, the knob 36 and the inner lead screw 30 may be replaced with other coupling mechanisms such as a rack and pinion. Although in the embodiments shown herein, a split nut 64 is used to selectively couple the knob 36 with an outer lead screw 32, the invention contemplates other selective coupling mechanisms. For example, in other embodiments, the split nut 64 and the outer lead screw 32 may be replaced with other selective coupling mechanisms such as a rack and pinion actuated with a lever similar to the lever 69.

Although the invention herein has been described with reference to particular embodiments in which a collapsible mitral valve is deployed into the native mitral annulus of a patient, it is to be understood that the invention contemplates embodiments in which the delivery device 10 is used to deploy other self-expanding medical implants. For example, the delivery device 10 may be used to deploy a collapsible aortic valve into the native aortic annulus of a patient, or to deploy a collapsible stent into a patient.

Although the invention herein has been described with reference to particular embodiments in which the catheter assembly is inserted into the patient through the apex of the heart (i.e., transapical insertion), it is to be understood that the invention contemplates embodiments in which the catheter assembly 16 extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly 16 approaches the mitral valve from the upstream side as well as from the downstream side of the valve.

It will be appreciated that the various dependent claims and the features set forth therein can be combined in different ways than presented in the initial claims. It will be appreciated that any of the features described in connection with individual embodiments may be shared with others of the described embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In summary, the disclosure herein recites multiple embodiments to summarize the foregoing. Described herein is a delivery device for a collapsible prosthetic heart valve. The delivery device may include a catheter assembly and an operating handle coupled to the catheter assembly. The catheter assembly may include an inner shaft around which a compartment is defined, and a distal sheath having a proximal segment and a distal segment together configured to enclose the compartment. The operating handle may include a housing defining a movement space therein, a first lead screw fixedly coupled to the proximal segment of the distal sheath and moveable in first and second opposite longitudinal directions within the movement space, a second lead screw coupled to the distal segment of the distal sheath and moveable in the first and second longitudinal directions within the movement space, a knob coupled to the housing and rotatable relative to the housing, the knob being threadedly engaged with the first lead screw, and a coupling assembly. The coupling assembly may have a first condition in which rotation of the knob in one direction moves the first lead screw in the first longitudinal direction and does not move the second lead screw in the first or second longitudinal directions, and a second condition in which rotation of the knob in the one direction simultaneously moves the first lead screw in the first longitudinal direction and the second lead screw in the second longitudinal direction; and/or the second lead screw may have an elongated bore configured to receive at least a portion of the first lead screw therein; and/or the coupling assembly may be configured to be selectively threadedly engaged with and disengaged from the second lead screw; and/or in the first condition of the coupling assembly, rotation of the knob in another direction opposite the one direction may move the first lead screw in the second longitudinal direction and may not move the second lead screw in the first or second longitudinal directions, and in the second condition of the coupling assembly, rotation of the knob in the another direction may simultaneously move the first lead screw in the second longitudinal direction and the second lead screw in the first longitudinal direction; and/or the coupling assembly may include a split nut having a plurality of threaded split nut portions, the split nut portions each being slideable away from one another and away from the second lead screw, the split nut having an engaged position in which threads of the split nut portions are engaged with the second lead screw and a disengaged position in which the threads of the split nut portions do not engage the second lead screw; and/or the inner shaft may be fixedly coupled to the distal segment of the distal sheath and removably coupled to the second lead screw; and/or the coupling assembly may include an interference member that in the first condition of the coupling assembly limits movement of the first lead screw in the first longitudinal direction from an initial position to a limit position, and that in the second condition of the coupling assembly permits movement of the first lead screw in the first longitudinal direction beyond the limit position; and/or the coupling assembly may include a releasable lock that in the first condition of the coupling assembly prevents movement of the second lead screw in the second longitudinal direction, and that in the second condition of the coupling assembly permits movement of the second lead screw in the second longitudinal direction; and/or the first lead screw may have external threads with a first pitch and the second lead screw may have external threads with a second pitch, the first pitch being different than the second pitch.

Also described herein is an operating handle for a delivery device for a collapsible prosthetic heart valve. The operating handle may include a housing defining a movement space therein, a first lead screw moveable in first and second opposite longitudinal directions within the movement space, a second lead screw moveable in the first and second longitudinal directions within the movement space, a knob coupled to the housing and rotatable relative to the housing, the knob being threadedly engaged with the first lead screw, and a coupling assembly. The coupling assembly may have a first condition in which rotation of the knob in one direction moves the first lead screw in the first longitudinal direction and does not move the second lead screw in the first or second longitudinal directions, and a second condition in which rotation of the knob in the one direction simultaneously moves the first lead screw in the first longitudinal direction and the second lead screw in the second longitudinal direction; and/or the second lead screw may have an elongated bore configured to receive at least a portion of the first lead screw therein; and/or the coupling assembly may be configured to be selectively threadedly engaged with and disengaged from the second lead screw; and/or in the first condition of the coupling assembly, rotation of the knob in another direction opposite the one direction may move the first lead screw in the second longitudinal direction and may not move the second lead screw in the first or second longitudinal directions, and in the second condition of the coupling assembly, rotation of the knob in the another direction may simultaneously move the first lead screw in the second longitudinal direction and the second lead screw in the first longitudinal direction; and/or the coupling assembly may include a split nut having a plurality of threaded split nut portions, the split nut portions each being slideable away from one another and away from the second lead screw, the split nut having an engaged position in which threads of the split nut portions are engaged with the second lead screw and a disengaged position in which the threads of the split nut portions do not engage the second lead screw; and/or the coupling assembly may include an interference member that in the first condition of the coupling assembly limits movement of the first lead screw in the first longitudinal direction from an initial position to a limit position, and that in the second condition of the coupling assembly permits movement of the first lead screw in the first longitudinal direction beyond the limit position; and/or the coupling assembly may include a releasable lock that in the first condition of the coupling assembly prevents movement of the second lead screw in the second longitudinal direction, and that in the second condition of the coupling assembly permits movement of the second lead screw in the second longitudinal direction; and/or the first lead screw may have external threads with a first pitch and the second lead screw may have external threads with a second pitch, the first pitch being different than the second pitch.

Further described herein is a method of delivering a collapsible prosthetic heart valve in a patient. The method may include providing a delivery device having a catheter assembly and an operating handle. The catheter assembly may include a compartment adapted to receive the valve in an assembled condition and a distal sheath slidable relative to the compartment. The operating handle may include a housing defining a movement space therein and first and second lead screws each movable in first and second opposite longitudinal directions within the movement space. The method may also include loading the valve into the compartment of the catheter assembly and covering the compartment and the valve with proximal and distal segments of the distal sheath, and inserting the catheter assembly into the patient so that the valve is positioned at a target location within the patient. The method may further include partially deploying the valve by moving the first lead screw in the first longitudinal direction within the movement space, and fully deploying the valve by simultaneously continuing movement of the first lead screw in the first longitudinal direction within the movement space and moving the second lead screw in the second longitudinal direction within the movement space; and/or the method may include, after partially deploying the valve, coupling the movement of the first lead screw in the first longitudinal direction with the movement of the second lead screw in the second longitudinal direction; and/or the coupling step may include moving portions of a split nut into threaded engagement with external threads of the second lead screw; and/or the step of partially deploying the valve may include moving the first lead screw in the first longitudinal direction from an initial position to a limit position defined by an interference member, and the step of fully deploying the valve may include moving the interference member to enable the first lead screw to move in the first longitudinal direction beyond the limit position; and/or the steps of partially deploying the valve and fully deploying the valve may be performed by rotating a knob in a single direction; and/or the collapsible prosthetic heart valve may be a self-expanding prosthetic mitral valve, the target location may be a native mitral valve annulus, and the step of partially deploying the valve may release anchor arms adjacent native mitral valve leaflets of the patient; and/or the step of partially deploying the valve may include moving the proximal segment of the distal sheath in a proximal direction to partially uncover the valve, and the step of fully deploying the valve may include moving the proximal segment of the distal sheath in the proximal direction and the distal segment of the distal sheath in the distal direction to completely uncover the valve; and/or the delivery device may include an inner shaft around which the compartment is defined, the inner shaft being fixedly coupled to the distal segment of the distal sheath and removably coupled to the second lead screw, and the method may include, after the step of fully deploying the valve, uncoupling the inner shaft from the second lead screw and moving the inner shaft relative to the housing to completely cover the compartment with the distal segment of the distal sheath; and/or the second lead screw may have an elongated bore configured to receive at least a portion of the first lead screw therein, and the steps of partially deploying the valve and fully deploying the valve may each include moving the first lead screw within the elongated bore of the second lead screw; and/or the step of fully deploying the valve may include moving the first lead screw a first distance in the first longitudinal direction and moving the second lead screw a second distance in the second longitudinal direction, the first distance being different than the second distance.

The invention claimed is:

1. A method of delivering a collapsible prosthetic heart valve in a patient, the method comprising:
providing a delivery device having a catheter assembly and an operating handle, the catheter assembly including a compartment adapted to receive the valve in an assembled condition and a distal sheath slidable relative to the compartment, the operating handle including a housing defining a movement space therein and first and second lead screws each movable in first and second opposite longitudinal directions within the movement space;
loading the valve into the compartment of the catheter assembly and covering the compartment and the valve with proximal and distal segments of the distal sheath;
inserting the catheter assembly into the patient so that the valve is positioned at a target location within the patient;
partially deploying the valve by moving the first lead screw in the first longitudinal direction within the movement space; and
fully deploying the valve by simultaneously continuing movement of the first lead screw in the first longitudinal direction within the movement space and moving the second lead screw in the second longitudinal direction within the movement space.

2. The method of claim 1, further comprising, after partially deploying the valve, coupling the movement of the first lead screw in the first longitudinal direction with the movement of the second lead screw in the second longitudinal direction.

3. The method of claim 2, wherein the coupling step includes moving portions of a split nut into threaded engagement with external threads of the second lead screw.

4. The method of claim 2, wherein the step of partially deploying the valve includes moving the first lead screw in the first longitudinal direction from an initial position to a limit position defined by an interference member, and the step of fully deploying the valve includes moving the interference member to enable the first lead screw to move in the first longitudinal direction beyond the limit position.

5. The method of claim 1, wherein the steps of partially deploying the valve and fully deploying the valve are performed by rotating a knob in a single direction.

6. The method of claim 1, wherein the collapsible prosthetic heart valve is a self-expanding prosthetic mitral valve, the target location is a native mitral valve annulus, and the step of partially deploying the valve releases anchor arms adjacent native mitral valve leaflets of the patient.

7. The method of claim 1, wherein the step of partially deploying the valve includes moving the proximal segment of the distal sheath in a proximal direction to partially uncover the valve, and the step of fully deploying the valve includes moving the proximal segment of the distal sheath in the proximal direction and the distal segment of the distal sheath in the distal direction to completely uncover the valve.

8. The method of claim 1, wherein the delivery device further includes an inner shaft around which the compartment is defined, the inner shaft being fixedly coupled to the distal segment of the distal sheath and removably coupled to the second lead screw, the method further comprising, after the step of fully deploying the valve, uncoupling the inner shaft from the second lead screw and moving the inner shaft relative to the housing to completely cover the compartment with the distal segment of the distal sheath.

9. The method of claim 1, wherein the second lead screw has an elongated bore configured to receive at least a portion of the first lead screw therein, and the steps of partially deploying the valve and fully deploying the valve each include moving the first lead screw within the elongated bore of the second lead screw.

10. The method of claim 1, wherein the step of fully deploying the valve includes moving the first lead screw a first distance in the first longitudinal direction and moving the second lead screw a second distance in the second longitudinal direction, the first distance being different than the second distance.

* * * * *